United States Patent [19]

Kulagowski

[11] Patent Number: 5,700,941
[45] Date of Patent: Dec. 23, 1997

[54] OCTAHYDRONAPHTHYRIDINE DERIVATIVES

[75] Inventor: Janusz Jozef Kulagowski, Bishops Stortford, United Kingdom

[73] Assignee: Merck, Sharp & Dohme, Ltd., Hoddesdon, England

[21] Appl. No.: 627,312

[22] Filed: Apr. 3, 1996

[30] Foreign Application Priority Data

Apr. 7, 1995 [GB] United Kingdom ............... 9507224

[51] Int. Cl.⁶ .................. C07D 471/08; A61K 31/445
[52] U.S. Cl. ................................ 546/122; 514/249
[58] Field of Search ............................ 546/122; 514/299

[56] References Cited

U.S. PATENT DOCUMENTS 4,786,642  11/1988  Teulon ............................. 514/300
5,576,319  11/1996  Baker et al. ...................... 514/253

OTHER PUBLICATIONS

Boyfield, I. et al.; N-(substituted-Phenyl) Piperazines: Antagonists with high binding and functional selectivity for dopamine $D_4$ receptors. Biorganic & Medicinal Chemistry Letters vol. 6, pp. 1227–1232, 1995.

*Primary Examiner*—C. Warren Ivy
*Assistant Examiner*—Charanjit S. Aulakh
*Attorney, Agent, or Firm*—Robert J. North; Melvin Winokur

[57] ABSTRACT

A class of substituted 1,2,3,4,5,6,7,8-octahydronaphthyridine derivatives are ligands for dopamine receptor subtypes within the body, in particular the $D_4$ subtype, and are therefore useful in the treatment and/or prevention of disorders of the dopamine system, in particular schizophrenia or depression.

9 Claims, No Drawings

OCTAHYDRONAPHTHYRIDINE DERIVATIVES

This invention relates to a particular class of heterocyclic compounds. More particularly, the invention is concerned with substituted octahydronaphthyridine derivatives which are ligands for dopamine receptor subtypes within the body, in particular the dopamine $D_4$ receptor subtype. They are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

By virtue of their activity as ligands for dopamine receptor subtypes within the body, the compounds in accordance with the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The compounds in accordance with the present invention, being ligands for dopamine receptor subtypes within the body, in particular the $D_4$ receptor subtype, are accordingly of use in the treatment and/or prevention of disorders of the dopamine system, including schizophrenia and depression.

The present invention provides a compound of formula I, or a salt or prodrug thereof:

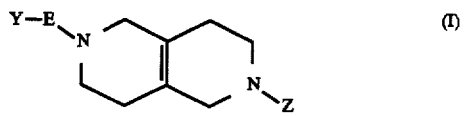

wherein

E represents a straight or branched alkylene chain containing from 1 to 4 carbon atoms; and Y and Z independently represent an optionally substituted aryl or heteroaryl group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where Y and/or Z in the compounds of formula I above represents an optionally substituted aryl group, this is suitably an optionally substituted phenyl or naphthyl group.

Where Y and/or Z represents an optionally substituted heteroaryl group, examples of suitable groups typically include optionally substituted pyridyl, quinolinyl, quinolonyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrrolo-pyridinyl, pyrazolyl, indazolyl, imidazolyl, benzimidazolyl, oxazolyl, isoxazolyl, oxadiazolyl, thiazolyl, isothiazolyl and thiadiazolyl groups.

The aryl or heteroaryl groups Y and/or Z may be optionally substituted by one or more groups suitably selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, $C_{1-3}$ alkylenedioxy, nitro, cyano, carboxy, $C_{2-6}$ alkoxycarbonyl, $C_{2-6}$ arkoxycarbonyl ($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphqnyl, $C_{1-6}$ alkylsulphonyl, arylsulphonyl, trifluoromethane-sulphonyloxy, —NR'R'', —NR'COR'', —NR''CO$_2$R'', —NR''SO$_2$R'', —CH$_2$NR''SO$_2$R'', —NHCONR'R'', —PO(OR'')(OR''), —CONR'R'', —SO$_2$NR'R'' and —CH$_2$SO$_2$NR'R'', in which R'' and R''' independently represent hydrogen, $C_{1-6}$ alkyl, aryl or aryl ($C_{1-6}$) alkyl.

As used herein, the expression "$C_{1-6}$ alkyl" relates to methyl and ethyl groups, and straight-chained or branched propyl, butyl, pentyl and hexyl groups. Particular alkyl groups include methyl, ethyl, n-propyl, isopropyl and t-butyl. Derived expressions such as "$C_{1-6}$ alkoxy" are to be construed accordingly.

The term "halogen" as used herein includes fluorine, chlorine, bromine and iodine, especially fluorine or chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The alkylene chain E in the compounds of formula I above may be, for example, methylene, ethylene, 1-methylethylene, propylene or 2-methylpropylene. In a favoured embodiment, E represents a methylene linkage.

Examples of optional substituents on the aryl or heteroaryl groups Y and/or Z suitably include $C_{1-6}$ alkyl, halogen, cyano, nitro, trifluoromethyl, $C_{1-6}$ alkoxy, $C_{1-3}$ alkylenedioxy, di($C_{1-6}$)alkylamino and aryloxy.

Particular values for the group Y include phenyl, quinolin-3-yl, 2(1H)-quinolon-8-yl, indol-2-yl, indol-3-yl, pyrrolo[2,3-b]pyridin-3-yl, benzofuran-3-yl, indazol-3-yl and benzimidazol-3-yl, especially phenyl or pyrrolo[2,3-b]pyridin-3-yl.

Particular values for the group Z include phenyl, methylphenyl, ethylphenyl, fluorophenyl, chlorophenyl, bromophenyl, iodophenyl, difluorophenyl, dichlorophenyl, cyanophenyl, trifluoromethyl-phenyl, methoxyphenyl, ethoxyphenyl, methylene dioxyphenyl, dimethylamino-phenyl, phenoxyphenyl, pyridinyl, methylpyridinyl, chloropyridinyl, isoquinolinyl, indolyl, methylindolyl, indazolyl and benzthienyl.

One sub-class of compounds according to the invention is represented by the compounds of formula IIA, and salts and prodrugs thereof:

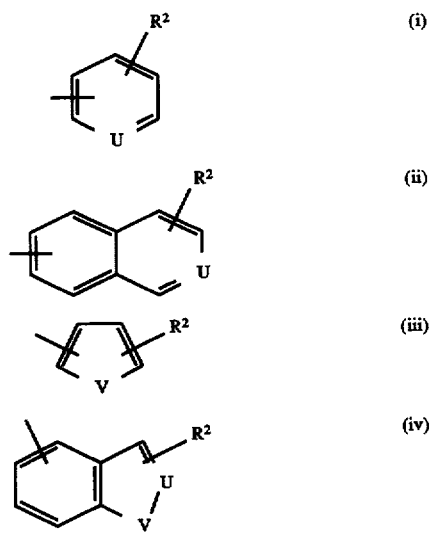
(IIA)

wherein n is 1, 2 or 3, preferably 1;

$Z^1$ represents a group of formula (i), (ii), (iii), (iv) or (v):

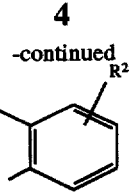
(i)

(ii)

(iii)

(iv)

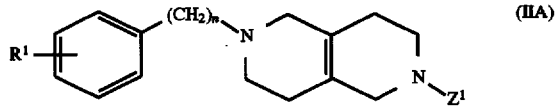
(v)

in which U represents CH or N;

V represents oxygen, sulphur, NH or N-methyl; and $R^1$ and $R^2$ independently represent hydrogen, halogen, cyano, nitro, trifluoromethyl, $C_{1-6}$ alkyl, $C_{1-6}$ alkoxy or di($C_{1-6}$)alkylamino.

Particular values of $R^1$ and/or $R^2$ include hydrogen, fluoro, chloro, cyano, nitro, trifluoromethyl, methyl, methoxy and dimethylamino.

In relation to formula IIA above, $R^1$ is suitably hydrogen.

In a typical embodiment of the compounds of formula IIA above, $Z^1$ represents a group of formula (i) as defined above wherein U is CH and $R^2$ is hydrogen.

Another sub-class of compounds according to the invention is represented by the compounds of formula IIB, and salts and prodrugs thereof:

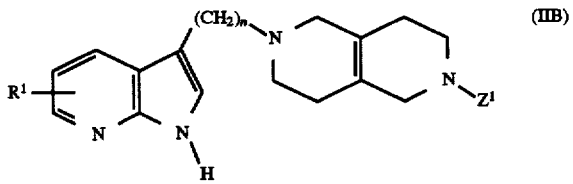
(IIB)

wherein n, $Z^1$ and $R^1$ are as defined with reference to formula IIA above.

In relation to formula IIB, $R^1$ is suitably hydrogen.

Specific compounds within the scope of the present invention include:

2-benzyl-6-phenyl-1,2,3,4,5,6,7,8-octahydro[2,6] naphthyridine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia or depression, a suitable dosage level is about 0.001 to 250 mg/kg per day, preferably about 0.005 to 100 mg/kg per day, and especially about 0.01 to 5 mg/kg per day. The compounds may be administered on a regimen of 1 to 4 times per day.

In order to alleviate the symptoms of schizophrenia without causing sedation or extrapyramidal side-effects, it is believed that the dosage level of the active ingredient should be selected such that the dose administered is effective in substantially completely blocking the dopamine $D_4$ receptor subtype in human brain whilst displaying no or negligible $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds in accordance with this invention may be co-administered with another medicament, for example a known anti-schizophrenic agent which produces its effects via dopamine $D_2$ and/or $5-HT_2$ receptor blockade. Such co-administration may be desirable where a patient is already on an established treatment regime, for example one involving conventional anti-schizophrenic medicaments such as haloperidol or chlorpromazine.

The compounds in accordance with the present invention may be prepared by a process which comprises reducing a compound of formula III:

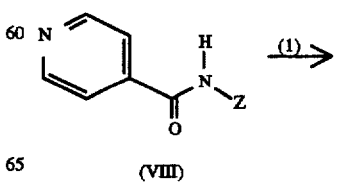

wherein E, Y and Z are as defined above.

A suitable reducing agent for effecting the reduction of compound III is alane ($AlH_3$). This reagent is conveniently generated in situ by treatment of lithium aluminium hydride with aluminium chloride, typically in an inert solvent such as tetrahydrofuran.

In an alternative procedure, the compounds according to the present invention may be prepared by a process which comprises reacting a compound of formula IV with a compound of formula V:

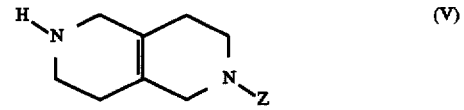

wherein E, Y and Z are as defined above, and L represents a suitable leaving group.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as toluene, typically at the reflux temperature of the solvent.

The compounds of formula V above may be prepared by deprotection of a compound of formula VI:

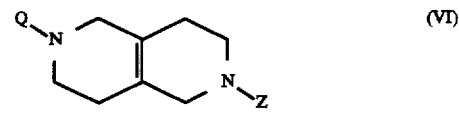

wherein Z is as defined above, and Q represents an amino-protecting group.

The amino-protecting group Q is suitably benzyl, which can conveniently be removed as necessary by treating compound VI with 1-chloroethyl chloroformate in a solvent such as dichloromethane, followed by heating under reflux in methanol.

The intermediates of formula VI above may be prepared by reduction of the corresponding compound of formula VII:

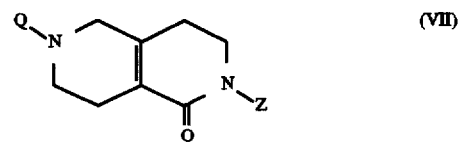

wherein Z and Q are as defined above; under conditions analogous to those described above in relation to compound III.

Where Q represents benzyl, the preparation of a typical intermediate of formula VII is illustrated by the following reaction scheme:

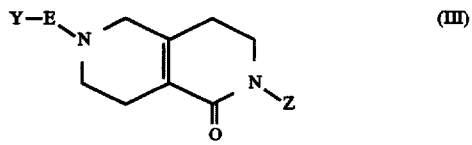

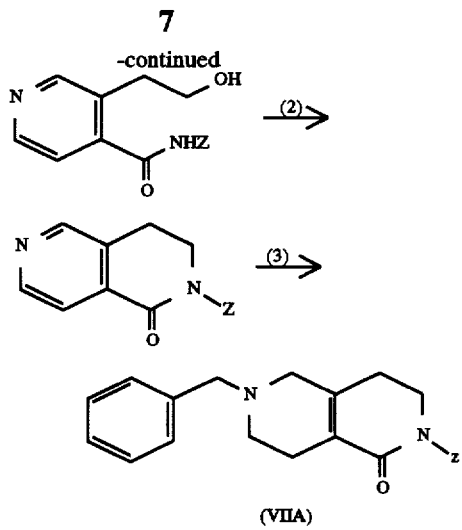

(VIIA)

wherein Z is as defined above.

Step 1 of the reaction scheme involves treatment of the starting material VIII with n-butyllithium, followed by reaction of the resulting anionic species with ethylene oxide. In Step 2, the hydroxyethylpyridine derivative thereby obtained is cyclised using triphenylphosphine and diethyl azodicarboxylate, typically in tetrahydrofuran. Step 3 comprises formation of the benzylpyridinium species by reaction with benzyl bromide in refluxing toluene, followed by reduction to the corresponding octahydronaphthyridine analogue VIIA using sodium borohydride.

The intermediates of formula III above may be prepared by reacting a compound of formula IV as defined above with a compound of formula IX:

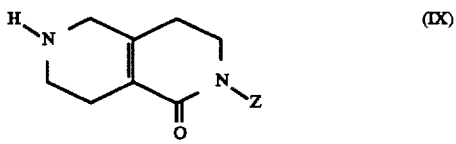

wherein Z is as defined above; under conditions analogous to those described above in relation to the reaction between compounds III and IV.

The intermediates of formula IX may in turn be prepared by deprotection of a compound of formula VII as defined above, under conditions analogous to those described in relation to the deprotection of compound VI.

Where they are not commercially available, the starting materials of formula IV and VIII may be prepared by standard methods well known from the art.

It will be appreciated that any compound of formula I initially obtained from any of the above processes may, where appropriate, subsequently be elaborated into a further desired compound of formula I using techniques known from the art. Indeed, as will be appreciated, the compounds of formula VI wherein Q is benzyl are compounds according to the invention in their own right.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The following Example illustrates the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compound of the accompanying Example was tested in the above assay, and was found to possess a $K_i$ value for displacement of [$^3$H]-spiperone from the human dopamine $D_4$ receptor subtype of below 1.5 μM.

EXAMPLE 1

2-Benzyl-6-phenyl-1,2,3,4,5,6,7,8-octahydro[2,6] naphthyridine

Step 1: 3-(2-Hydroxyethyl)-N-phenylisonicotinamide

To a solution of N-phenylisonicotinamide (1.98 g, 10 mmol) in tetrahydrofuran (40 ml) at −78° C. was added a solution of n-butyllithium (1.6M in hexanes; 13.5 ml, 21.6 mmol) and the resulting red solution stirrred for 40 minutes before addition of a solution of ethylene oxide in dioxane (3.56M; 3.0 ml, 11 mmol). After allowing the mixture to warm to room temperature over 2½ hours, the reaction was quenched by addition of methanol (8 ml). The solvent was evaporated and the residue partitioned between ethyl acetate (70 ml) and water (25 ml). The organic layer was washed with saturated brine (25 ml), dried ($MgSO_4$) and evaporated. The residue was chromatographed on silica eluting with 10% methanol/dichloromethane to afford the title compound as a solid (1.05 g, 43%); $\delta_H$ ($CDCl_3$) 3.07 (2H, t, J 5.6 Hz, $ArCH_2CH_2OH$), 3.70 (1H, br s, OH), 4.10 (2H, t, J 5.6 Hz, $ArCH_2CH_2OH$), 7.15–7.19 (1H, m, ArH), 7.35–7.39 (2H, m, ArH), 7.49 (1H, d, J 5.2 Hz, ArH), 7.69–7.71 (2H, m, ArH), 8.44–8.48 (2H, m, ArH), 9.77 (1H, s, NH).

Step 2: 2-Phenyl-3,4-dihydro-2H-[2,6]naphthyridine-1-one

To a solution of the foregoing amide (1.58 g, 6.5 mmol) and triphenylphosphine (1.83 g, 7 mmol) in tetrahydrofuran (60 ml) was added diethyl azodicarboxylate (1.10 ml, 7 mmol) and the solution stirred for 3 hours. The solvent was evaporated, the residue redissolved in ethyl acetate (50 ml) and the solution washed with hydrochloric acid (1M, 5×10 ml). The combined acidic washings were basified with aqueous sodium hydroxide (4M) and the resultant suspension extracted with dichloromethane (4×10 ml). The combined organic extracts were dried (MgSO$_4$) and evaporated in vacuo to give an oil which solidified on standing. Recrystallisation from ethyl acetate gave the title compound as white needles (838 mg, 58%); $\delta_H$ (CDCl$_3$) 3.11 (2H, t, J 6.5 Hz, 4-CH$_2$), 3.98 (2H, t, J 6.5 Hz, 3-CH$_2$), 7.19–7.39 (5H, m, ArH), 7.88 (1H, d, J 4.9 Hz, 8-H), 8.56 (1H, s, 5-H), 8.64 (2H, d, J 4.9 Hz, 7-H).

Step 3: 6-Benzyl-2-phenyl-3,4,5,6,7,8-hexahydro-2H-[2,6]naphthyridin-1-one

The foregoing naphthyridine (835 mg, 3.73 mmol) in toluene (25 ml) was refluxed with benzyl bromide (0.48 ml, 4 mmol) for 24 hours and then left to stand overnight. The solid was filtered off, dissolved in methylated spirit (30 ml) and sodium borohydride (152 mg, 4mmol) added in portions. The reaction was stirred for 4 hours, the resultant suspension filtered and the filtrate evaporated. The residue was partitioned between ethyl acetate (2×25 ml) and water (50 ml). The combined organics were dried (MgSO$_4$) and evaporated in vacuo. The residue was chromatographed on silica eluting with 80% ethyl acetate/hexanes to give the title compound as a pale yellow gum (867 mg, 73%); $\delta_H$ (CDCl$_3$) 2.33–2.36 (2H, m, naphthyridinyl H's), 2.47–2.48 (2H, m, naphthyridinyl H's), 2.67 (2H, t, J 5.8 Hz, 4-CH$_2$), 3.08 (2H, br s, naphthyridinyl H's), 3.65 (2H, s, PhCH$_2$N), 3.81 (2H, t, J 5.8 Hz, 3-CH$_2$), 7.15–7.37 (10H, m, ArH).

Step 4: 2-Benzyl-6-phenyl-1,2,3,4,5,6,7,8-octahydro[2,6]-naphthyridine

To a solution of aluminium chloride (0.12 g, 0.9 mmol) in tetrahydrofuran (10 ml) was added a solution of lithium aluminium hydride (1M in tetrahydrofuran; 2.5 ml, 2.5 mmol) and the resulting solution stirred for 10 minutes. To this was added a solution of the foregoing amide (665 mg, 2.1 mmol) in tetrahydrofuran (6 ml) and the reaction mixture stirred for 3 hours. The reaction was quenched by careful addition of methanol (0.5 ml) and water (0.45 ml). The resulting suspension was stirred for 30 minutes, filtered and the filtrate evaporated. The residue was chromatographed on silica eluting with 35% ethyl acetate/petrol (60°–80°) to afford the title compound (448 mg, 71%) as a gum. A portion of this material was characterized by preparing the oxalate salt as buff needles, m.p. 135° C. (dec.) (methanol-ether); (Found: C, 69.60; H, 6.81; N, 6.97. C$_{21}$H$_{24}$N$_2$.C$_2$H$_2$O$_4$ requires C, 70.03; H, 6.64; N, 7.10%); $\delta_H$ (d$_6$-DMSO) 2.06 (2H, br s, naphthyridinyl H's), 2.24 (2H, br s, naphthyridinyl H's), 3.04 (2H, br s, naphthyridinyl H's), 3.27–3.33 (4H, m, naphthyridinyl H's), 3.55 (2H, br s, naphthyridinyl H's), 4.07 (2H, s, PhCH$_2$N), 6.74 (1H, t, J 7.3 Hz, ArH), 6.93 (2H, d, J 8.0 Hz, ArH), 7.20 (2H, t, J 8.6 Hz, ArH), 7.40–7.44 (5H, m, ArH).

I claim:

1. A compound of formula I, or a salt or prodrug thereof:

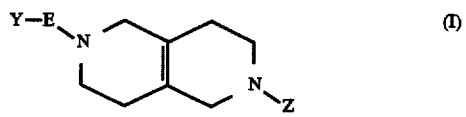

wherein

E represents a straight or branched alkylene chain containing from 1 to 4 carbon atoms; and Y and Z independently represent an optionally substituted aryl or heteroaryl group.

2. A compound as claimed in claim 1 wherein E represents a methylene linkage.

3. A compound as claimed in claim 1 wherein Y represents phenyl, quinolin-3-yl, 2(1H)-quinolon-3-yl, indol-2-yl, indol-3-yl, pyrrolo[2,3-b]pyridin-3-yl, benzofuran-3-yl, indazol-3-yl or benzimidazol-3-yl.

4. A compound as claimed in claim 1 wherein Z represents phenyl, methylphenyl, ethylphenyl, fluorophenyl chlorophenyl, bromophenyl, iodophenyl, difluorophenyl, dichlorophenyl, cyanophenyl, trifluoromethyl-phenyl, methoxyphenyl, ethoxyphenyl, methylenedioxyphenyl, dimethylamino-phenyl, phenoxyphenyl, pyridinyl, methylpyridinyl, chloropyridinyl, isoquinolinyl, indolyl, methylindolyl, indazolyl or benzthienyl.

5. A compound as claimed in claim 1 represented by formula IIA, and salts and prodrugs thereof:

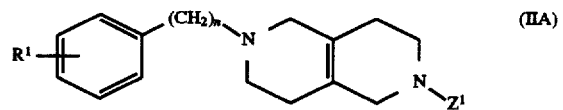

wherein n is 1, 2 or 3;

Z$^1$ represents a group of formula (i), (ii), (iii), (iv) or (v):

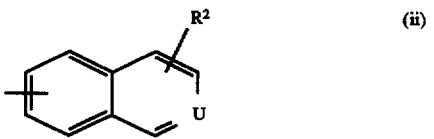

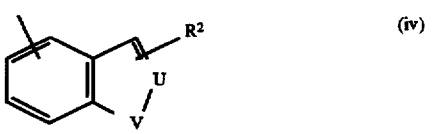

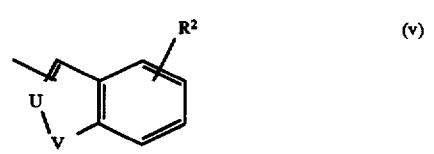

in which U represents CH or N;

V represents oxygen, sulphur, NH or N-methyl; and $R^1$ and $R^2$ independently represent hydrogen, halogen, cyano, nitro, trifluoromethyl, $C_{1-6}$ alkyl, $C_{1-6}$ alkoxy or di($C_{1-6}$)alkylamino.

6. A compound as claimed in claim 5 wherein $Z^1$ represents a group of formula (i) in which U is CH and $R^2$ is hydrogen.

7. A compound as claimed in claim 1 represented by formula IIB, and salts and prodrugs thereof:

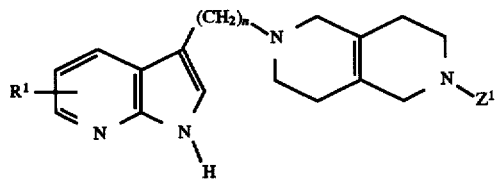

(IIB)

wherein n, $Z^1$ and $R^1$ are as defined in claim 5.

8. A compound selected from:

2-benzyl-6-phenyl-1,2,3,4,5,6,7,8-octahydro[2,6]naphthyridine;

and salts and prodrugs thereof.

9. A pharmaceutical composition comprising a compound of formula I as defined in claim 1, or a pharmaceutically acceptable salt thereof or a prodrug thereof, in association with a pharmaceutically acceptable carrier.

* * * * *